US00PP21329P2

(12) United States Plant Patent
Sacks et al.

(10) Patent No.: US PP21,329 P2
(45) Date of Patent: Sep. 28, 2010

(54) ***PHLOX* PLANT NAMED 'TRIPLE PLAY'**

(50) Latin Name: ***Phlox glaberrima* ssp. *triflora***
Varietal Denomination: Triple Play

(76) Inventors: Janet L. Sacks, 337 Acton St., Carlisle, MA (US) 01741-1432; Martin C. Schafer, 337 Acton St., Carlisle, MA (US) 01741-1432

( * ) Notice: Subject to any disclaimer, the term of this patent is extended or adjusted under 35 U.S.C. 154(b) by 0 days.

(21) Appl. No.: 12/586,010

(22) Filed: Sep. 16, 2009

(51) Int. Cl.
*A01H 5/00* (2006.01)

(52) U.S. Cl. ..... Plt./320

(58) Field of Classification Search ..... Plt./320
See application file for complete search history.

*Primary Examiner*—Annette H Para
(74) *Attorney, Agent, or Firm*—Penny J. Aguirre

(57) ABSTRACT

A new cultivar of *Phlox*, 'Triple Play', characterized by its flowers that are pink in color with a darker pink eye zone, its variegated foliage with green centers and a creamy white margins that are flushed with pink when grown under cool temperatures (spring and autumn), its short stature, and its cold hardiness at least to U.S.D.A. Zone 5.

2 Drawing Sheets

Botanical Classification: *Phlox glaberrima* ssp. *triflora*.
Cultivar designation: 'Triple Play'.

BACKGROUND OF THE INVENTION

The present invention relates to a new and distinct cultivar of *Phlox* plant, botanically known as *Phlox glaberrima* ssp. *triflora* 'Triple Play' and will be referred to hereafter by its cultivar name, 'Triple Play'. The new cultivar represents a new herbaceous perennial grown for landscape use.

The Inventors discovered the new cultivar, 'Triple Play', in their garden in Carlisle, Mass. in September of 2002. 'Triple Play' originated as a single variegated basal stem mutation on an unnamed plant of *Phlox glaberrima* ssp. *triflora*.

Asexual reproduction of the new cultivar was first accomplished by stem layering in Carlisle, Mass. in September of 2002 by the Inventors. Propagation by stem layering and stem cuttings has determined that the characteristics of this cultivar are stable and are reproduced true to type in successive generations.

SUMMARY OF THE INVENTION

The following traits have been repeatedly observed and represent the characteristics of the new cultivar for a period of six years. These attributes in combination distinguish 'Triple Play' from other varieties of *Phlox* known to the Inventors 1. 'Triple Play' exhibits flowers that are pink in color with a darker pink eye zone.
2. 'Triple Play' exhibits variegated foliage with green centers and creamy white margins that are flushed with pink when grown under cool temperatures (spring and autumn).
3. 'Triple Play' matures to a shorter height than is typical of the species.
4. 'Triple Play' is hardy at least to U.S.D.A. Zone 5.

'Triple Play' differs from its parent variety in having variegated foliage. In addition, the 'Triple Play' is shorter in height, maturing to about 38 cm in height with the parent plant maturing to 60 cm to 75 cm in height. The new cultivar is most similar in plant habit and flower form to the cultivar

*Phlox glaberrima* 'Morris Berd' (not patented). 'Triple Play' is comparable in having a similar growth habit and flower color. 'Triple Play' differs in having variegated foliage and a more compact growth habit. The new cultivar may also be compared to *Phlox stolonifera* 'Variegata' (not patented). 'Variegata' is similar in having variegated foliage, however, 'Variegata' differs from 'Triple Play' in being a cultivar of a different species, in having a vigorous stoloniferous habit, blooming about four weeks earlier, exhibiting leaves that are more rounded, and in being shorter in height.

BRIEF DESCRIPTION OF THE DRAWING

The accompanying colored photographs illustrate the overall appearance and distinct characteristics of the new *Phlox*. The photographs were taken in June 2008 of two year-old plants of 'Triple Play' as grown outdoors in a garden in Carlisle, Mass. The photograph in FIG. 1 is a view of a plant of 'Triple Play' in bloom. The photograph in FIG. 2 is a close-up view of the flowers of 'Triple Play'. The Photograph in FIG. 3 provides a close-up view of the foliage in spring. The colors in the photograph may differ slightly from the color values cited in the detailed botanical description, which accurately describe the colors of the new *Phlox*.

DETAILED BOTANICAL DESCRIPTION OF THE PLANT

Figure 1:
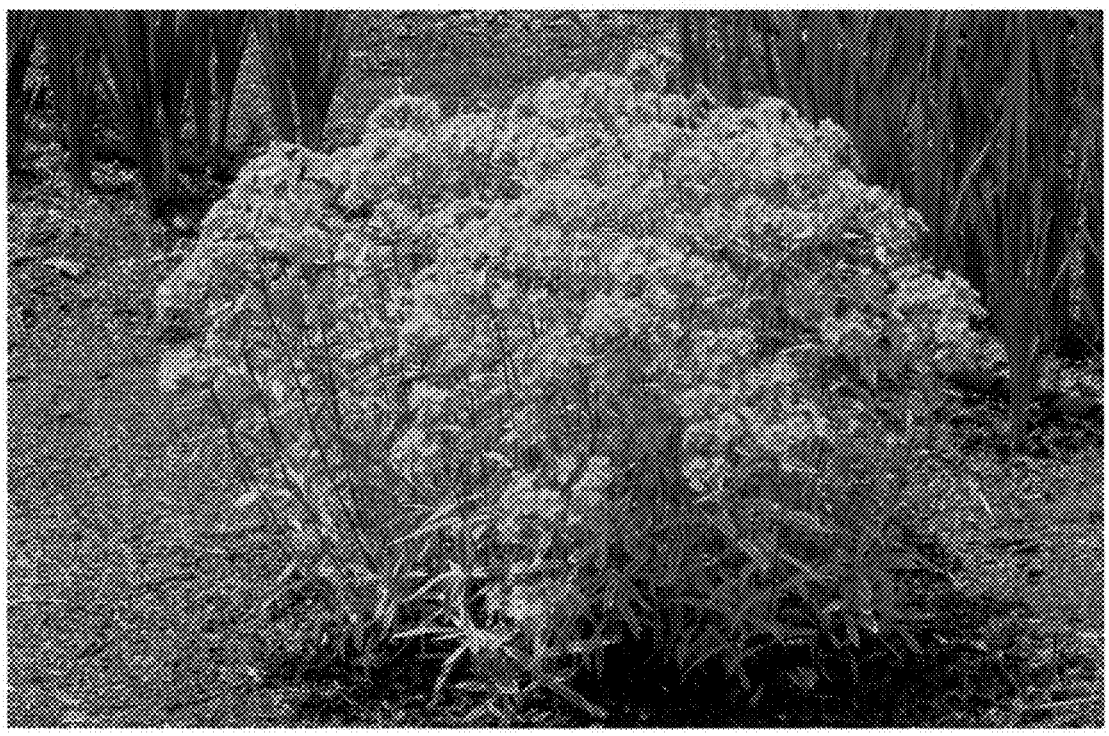
Figure 2:
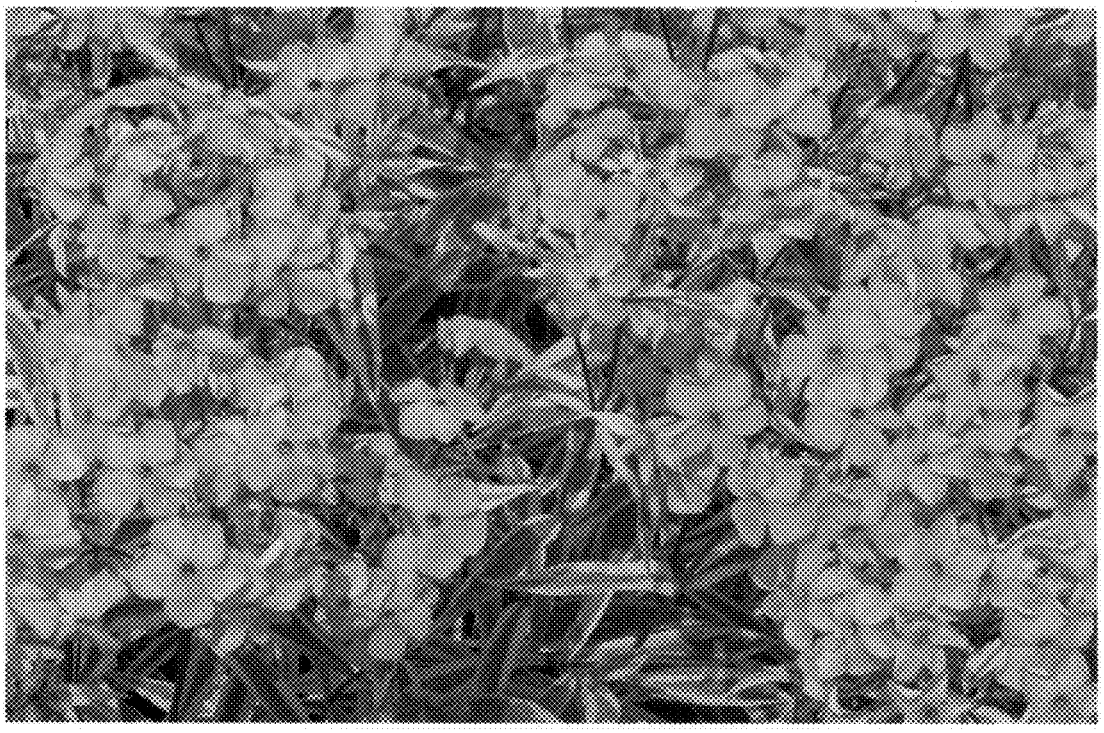
Figure 3:
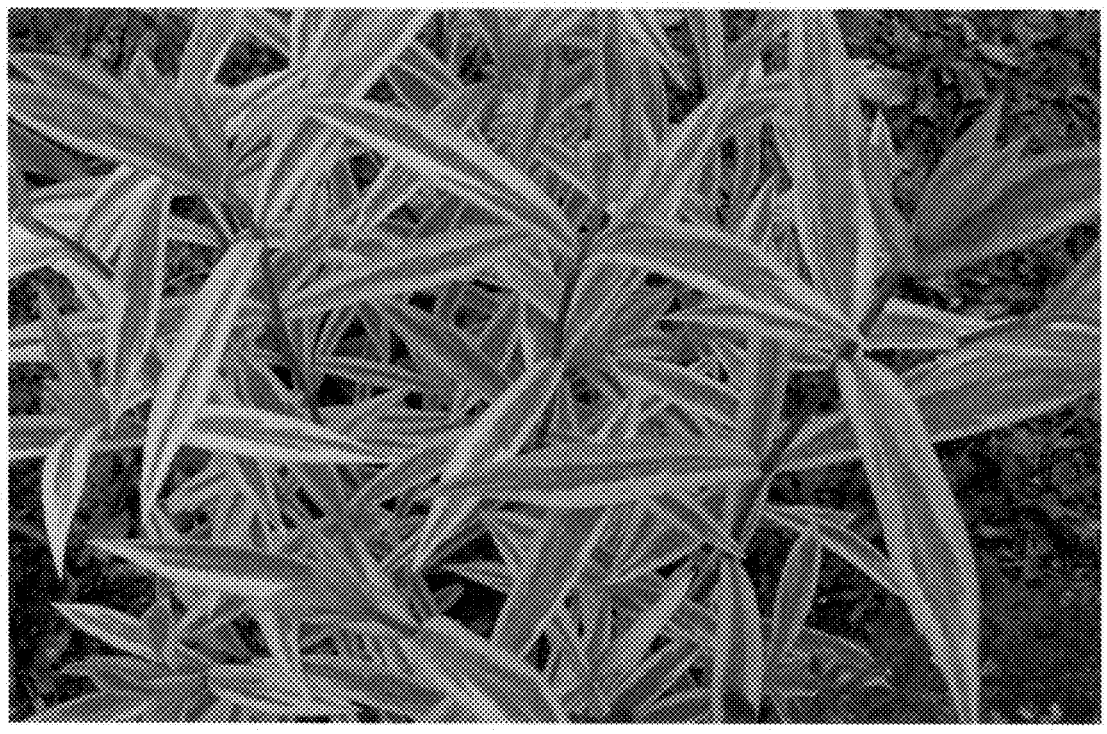

The following is a detailed description of two year-old plants of the new cultivar as grown outdoors in a garden in Carlisle, Mass. The phenotype of the new cultivar may vary with variations in environmental, climatic, and cultural conditions, as it has not been tested under all possible environmental conditions. The color determination is in accordance with The 2007 RHS Colour Chart of the Royal Horticultural Society, London, England, except where general color terms of ordinary dictionary significance are used.

*Blooming period.*—3 to 4 weeks in mid June in Massachusetts.

*Plant habit.*—Herbaceous perennial, upright.

*Height and spread.*—Reaches about 38 cm in height and about 20 cm to 38 cm in spread.

*Cold hardiness.*—At least in U.S.D.A. Zone 5.

*Diseases and pests.*—No susceptibility or resistance to diseases or pests has been observed.

*Root description.*—Fine, fibrous.

*Branching habit.*—Flowering stems branch freely from the basal foliage.

Growth and propagation:

*Growth rate.*—Moderately vigorous.

*Propagation.*—Stem cuttings, division or stem layering.

Stem description:

*Stem size.*—Flowering stem; an average of 34 cm in length and 1.8 mm in width, basal leaves (non-flowering); an average of 11 cm in length and 2 mm in width.

*Stem shape.*—Oval.

*Stem color.*—A blend of 197B and 194A with basal stem suffused with 187B.

*Stem surface.*—Finely puberulent.

*Stem aspect.*—Held nearly upright.

*Internode length.*—An average of 2.8 cm on lower nodes and 5 cm on upper nodes.

Foliage description:

*Leaf shape.*—Elliptic to oblanceolate.

*Leaf division.*—Simple.

*Leaf base.*—Attenuate.

*Leaf apex.*—Acuminate.

*Leaf venation.*—Pinnate, not conspicuous, vein color matches leaf color.

*Leaf margins.*—Entire.

*Leaf attachment.*—Sessile.

*Leaf arrangement.*—Opposite.

*Leaf surface.*—Smooth and finely puberulent on upper and lower surface.

*Leaf color.*—Upper surface newly formed and mature; centers 138A and margins a color between 11C and 11D, lower surface newly formed and mature; centers range from 191A to 191B and margins a color between 11C and 11D, in cooler seasons the margins become flushed with 70B and 70C.

*Leaf size.*—Flowering stems; an average of 5 cm in length and 1.8 cm in width, basal; up to 6 cm in length and 1.8 cm in width.

*Leaf quantity.*—An average of 18 per flowering branch and 22 per basal branch.

*Leaf fragrance.*—None.

Flower description:

*Inflorescence type.*—Panicles of 6 flowers on terminus of stem and 1 to 3 flowers per lateral branch with 4 lateral branches per stem.

*Lastingness of inflorescence.*—About 3 to 4 weeks from the opening of the first flower to senescence of last flower dependant on climactic conditions.

*Inflorescence size.*—An average of 9 cm in height and 12 cm in diameter (including peduncles).

*Flower fragrance.*—Mild *phlox* fragrance.

*Flower number.*—Average of 15 per inflorescence, one inflorescence per flowering stem.

*Flower aspect.*—Upright to horizontal, dependant on location of the inflorescence.

*Flower bud.*—An average of 2.5 cm in length and up to 6 mm in width, with petal portion conical in shape and a blend of 85A and 85D in color with margins of petals N88B.

*Flower form.*—Explanate with base tubular.

*Flower size.*—An average of 2.5 cm in length and 1.8 cm in width.

*Corolla tube.*—About 1.9 cm in length, 3 mm in width, a blend of N80B and N80C in color, very finely puberulent surface.

*Corolla lobes.*—5, orbicular in shape, held horizontally when fully open, touching and occasionally overlapping, about 1 cm in length and width, apex rounded, base fused to tube, entire margins, upper surface color; a blend of N80B to 81B with markings on eye ring 71D, lower surface color; a blend of N80D and N155B, surface very finely puberulent on upper and lower surface.

*Calyx.*—Campanulate in form, comprised of fused sepals with sepal tips free, an average of 1 cm in length and 4 mm in width.

*Sepals.*—5, primarily fused with free tips, linear to oblanceolate in shape, margins entire and slightly ciliate, base fused, apex attenuate, an average of 1 cm in length and 2 mm in width, surface is finely puberulent, color is 4D with stripes and base 144D and speckled with N77B.

*Peduncles.*—Oval in shape, an average of 7.5 cm in length on lower flowers and 2.5 cm in length on upper cymes, an average of 1.2 mm in width, puberulent surface, color a blend of 197B and 194A.

*Pedicels.*—Oval in shape, an average of 4 mm in length and 1 mm in width, puberulent surface, color a blend of 144A, 197B and 194A.

Reproductive organs:

*Gynoecium.*—1 pistil, stigma has 3 linear branches about 2 mm in length and 8A in color, style is about 1 cm in length, less than 1 mm in width, and 145C in color, ovary is inferior, 2 mm in length, 1.2 mm in width, oblong in shape and 145B in color.

*Androcoecium.*—5 stamens, protanderous, anthers are dorsifixed, thread-like in shape, and 1.5 mm in length, 11A in color, filaments are adnate to corolla, 3 mm in length, 85D in color, pollen is abundant and 13A in color.

*Seeds.*—Not observed.

It is claimed:

1. A new and distinct cultivar of *Phlox* plant named 'Triple Play' as herein illustrated and described.

* * * * *